United States Patent
Lushka et al.

(10) Patent No.: US 12,390,414 B1
(45) Date of Patent: *Aug. 19, 2025

(54) LIP COMPOSITIONS

(71) Applicant: L'ORÉAL, Paris (FR)

(72) Inventors: Monika Lushka, Towaco, NJ (US); Susan Ashley Desteno, Springfield, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/630,358

(22) Filed: Apr. 9, 2024

Related U.S. Application Data

(63) Continuation of application No. 18/129,719, filed on Mar. 31, 2023, now Pat. No. 11,986,550.

(51) Int. Cl.

| | | |
|---|---|---|
| *A61K 8/92* | (2006.01) | |
| *A45D 40/00* | (2006.01) | |
| *A61K 8/02* | (2006.01) | |
| *A61K 8/06* | (2006.01) | |
| *A61K 8/25* | (2006.01) | |
| *A61K 8/73* | (2006.01) | |
| *A61Q 1/06* | (2006.01) | |
| *A61Q 19/00* | (2006.01) | |

(52) U.S. Cl.
CPC ............ *A61K 8/922* (2013.01); *A45D 40/00* (2013.01); *A61K 8/0229* (2013.01); *A61K 8/06* (2013.01); *A61K 8/25* (2013.01); *A61K 8/731* (2013.01); *A61Q 1/06* (2013.01); *A61Q 19/001* (2013.01); *A61K 2800/30* (2013.01); *A61K 2800/31* (2013.01); *A61K 2800/34* (2013.01); *A61K 2800/43* (2013.01); *A61K 2800/87* (2013.01)

(58) Field of Classification Search
CPC .......... A61K 8/922; A61K 8/25; A61K 8/731; A61K 8/0229; A61K 8/06; A61K 2800/43; A61K 2800/31; A61K 2800/34; A61K 2800/87; A61K 2800/30; A61Q 1/06; A61Q 19/001; A45D 40/00

USPC ............................ 401/49, 68, 75; 424/63, 64
See application file for complete search history.

(56) References Cited

U.S. PATENT DOCUMENTS

| | | |
|---|---|---|
| 2015/0313818 A1 | 11/2015 | Stagg et al. |
| 2017/0246099 A1 | 8/2017 | Jager Lezer et al. |
| 2019/0262257 A1 | 8/2019 | Rosario-Meléndez et al. |
| 2020/0214950 A1 | 7/2020 | Fioleau et al. |
| 2022/0125703 A1 | 4/2022 | Wong et al. |
| 2022/0287946 A1 | 9/2022 | Frezza et al. |
| 2023/0000072 A1 | 1/2023 | Ftouni et al. |
| 2023/0000729 A1 | 1/2023 | Liu et al. |
| 2023/0047813 A1* | 2/2023 | Logalbo ............. A61K 8/678 |

FOREIGN PATENT DOCUMENTS

| | | |
|---|---|---|
| CN | 108720238 B | 9/2021 |
| EP | 1753392 B1 | 12/2008 |

OTHER PUBLICATIONS

International Search Report and Written Opinion for corresponding PCT Application No. PCT/US2024/013126, dated May 16, 2024.
Mintel ID No. 61445621, dated Nov. 23, 2018.
French Search Report, and Written Opinion, for corresponding French Application No. 2305820, dated Dec. 5, 2023.
Mario Badescu Skin Care, "Lip Balm," Mintel, Record ID 6144561, Nov. 23, 2018.

* cited by examiner

*Primary Examiner* — David J Walczak
(74) *Attorney, Agent, or Firm* — MEAGHER EMANUEL LAKS GOLDBERG & LIAO, LLP

(57) ABSTRACT

A lip composition is provided. The lip composition may include at least 40% by weight of one or more emollients, at least 20% by weight of waxes, the waxes including a hard wax and a soft wax, and a plurality of fillers including silica silylate and cellulose. The lip composition may be free of water and silicones, and may be vegan. The lip composition preferably includes no more than 6% by weight of fillers, and preferably includes no more than about 3% by weight of colorants.

15 Claims, No Drawings

LIP COMPOSITIONS

TECHNICAL FIELD

The present invention relates to lip compositions comprising at least one natural oil, at least one fatty alcohol wax and particles of at least one filler. Preferably, the lip compositions contain minimal amount of animal-derived ingredients and/or beeswax, or are free of such ingredients.

BACKGROUND

Many lip compositions contain animal derived ingredients or beeswax to achieve a desired texture. Because of growing concerns over how such ingredients may be obtained, many customers prefer to avoid cosmetics containing such ingredients, opting instead for products not relying upon such ingredients. However, without such ingredients (particularly beeswax), it can be difficult to obtain a creamy and desirable texture in a lip composition.

Further, conventional techniques do not result in, e.g., a clean, vegan, and silicone-free lip formulation containing low pigment coverage level, soft matte finish, and lip nourishing ingredients.

BRIEF SUMMARY

Various deficiencies in the prior art are addressed below by the disclosed compositions of matter and techniques.

In various aspects, a lip composition may be provided. The lip composition may include at least 40% by weight of one or more emollients. The lip composition may include at least 20% by weight of waxes, the waxes including a hard wax and a soft wax. The lip composition may include a plurality of fillers including silica silylate and cellulose. The lip composition may be free of water and silicones.

The lip composition may include a coloring agent, where the coloring agent is present in a total amount not more than 5% by weight of the lip composition, and the coloring agent may preferably be present in a total amount of not more than 3% by weight of the lip composition. The fillers may be present in a total amount of not more than 6% by weight of the lip composition. The fillers may consist of silica silylate and cellulose. The emollients may be present in a total amount of not less than 60% by weight of the lip composition. The emollients may include at least one saturated, branched hydrocarbon having a carbon chain that is at least 20 carbons in length. The emollients may include one or more ester oils in an amount of at least 25% by weight of the lip composition.

The lip composition may include: (i) at least 40% by weight of one or more emollients; (ii) at least 20% by weight of waxes, the waxes including a hard wax and a soft wax; (iii) not more than 6% by weight of fillers, the fillers consisting of silica silylate and cellulose; (iv) not more than 5% by weight of one or more coloring agents; and (v) less than 0.5% of other components, such as one or more additives or excipients.

The lip composition is preferably a vegan composition. The lip composition may be essentially free of silica. The lip composition may be free of perlite. The lip composition may be free of beeswax.

In various aspects, a method of providing a low coverage and matte finish to lips may be provided. The method may include applying an embodiment of the lip composition as disclosed herein to the lips.

In various aspects, a lipstick product may be provided. The lipstick product may include a glass or polymeric container having a main body and a cap or lid. A lip composition as disclosed herein may be disposed within the main body of the container.

It is to be understood that both the foregoing general description and the following detailed description are exemplary and explanatory only, and are not restrictive of the invention.

DETAILED DESCRIPTION OF THE INVENTION

The following description and drawings merely illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be only for illustrative purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or, unless otherwise indicated (e.g., "or else" or "or in the alternative"). Also, the various embodiments described herein are not necessarily mutually exclusive, as some embodiments can be combined with one or more other embodiments to form new embodiments.

The numerous innovative teachings of the present application will be described with particular reference to the presently preferred exemplary embodiments. However, it should be understood that this class of embodiments provides only a few examples of the many advantageous uses of the innovative teachings herein. In general, statements made in the specification of the present application do not necessarily limit any of the various claimed inventions. Moreover, some statements may apply to some inventive features but not to others. Those skilled in the art and informed by the teachings herein will realize that the invention is also applicable to various other technical areas or embodiments.

As used herein, the term "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% of the indicated number.

As used herein, the term "volatile" means having a flash point of less than about 100° C.

As used herein, the term "non-volatile" means having a flash point of greater than about 100° C.

As used herein, the term "anhydrous" means the compositions contain less than 1% water (by weight). Preferably, anhydrous compositions of the present invention contain less than 0.5% water, and preferably no water.

As used herein, the term "polymer" means a compound which is made up of at least two monomers.

As used herein, the term "substantially free of (a component)" means that the systems or compositions contain no appreciable amount of the component, for example, no more than about 1% by weight, or no more than about 0.5% by weight, or no more than about 0.3% by weight, such as no more than about 0.1% by weight, based on the weight of the composition.

As used herein, the term "essentially free of (a component)" means that the systems or compositions contain no appreciable amount of the component, for example, no more than about 0.1% by weight, or no more than about 0.01% by weight, based on the weight of the composition.

As used herein, the term "free" or "completely free of (a component)" as defined herein means that the systems or compositions do not contain the component in any measurable degree by standard means.

The compositions and methods of the present invention can "comprise," "consist of" or "consist essentially of" the essential elements and limitations of the invention described herein, as well as any additional or optional ingredients, components, or limitations described herein or otherwise useful. For purposes of the compositions and methods of the present invention where the invention "consists essentially of" the identified ingredients and/or process steps, the "basic and novel property" of such compositions and/or methods is "a clean, silicone-free lip formulation containing low pigment coverage level, soft matte finish, and lip nourishing ingredients," and in some embodiments, may be "a clear, vegan, silicone-free lip formulation containing low pigment coverage level, soft matte finish, and lip nourishing ingredients."

Lip Composition.

In various aspects, a lip composition may be provided. The lip composition may include at least 40% by weight of one or more emollients. The lip composition may include at least 20% by weight of waxes, the waxes including a hard wax and a soft wax. The lip composition may include a plurality of fillers including silica silylate and cellulose.

Emollients.

As used herein, the term "emollient" as used herein refers to a compound or mixture of compounds that adds or replaces natural oils in the skin, for example by maintaining the integrity of the hydrolipids of the skin. The emollient may be a polar emollient or a non-polar emollient.

As used herein, the term "polar emollient" means any emollient having at least one polar moiety. The emollient may be one or both of high and medium polarity oil soluble emollients. Non-limiting examples of polar emollients include, but are not limited to, esters, polyol esters, and polyol ethers such as linear or branched chained polyglycerol esters and polyglycerol ethers. For example, the emollient be chosen from or comprise caprylic/capric triglyceride, isopropyl myristate, PPG-3 myristyl ether, isopropyl palmitate, ethylhexyl palmitate, dibutyl adipate, propyleneglycol dicaprylate/dicaprate, cocoglyceride, cetearyl isononanoate, isopropyl myristate, isodecyl neopentanoate, tridecyl neopentanoate, C12-15 alkyl benzoate, isopropyl lauroyl sarsosinate, phenethyl benzoate, and mixtures thereof. Other examples of emollients include oil soluble emollients having high or medium polarity moieties.

The emollient may be a non-polar oil soluble emollient. As used herein, the term "non-polar emollient" means any emollient possessing no permanent electric moments. Non-limiting examples of non-polar emollients may include, but are not limited to, non-polar hydrocarbon, such as esters, linear or branched, or chained hydrocarbons. For example, the emollients may be chosen form or include paraffins, isoparaffins, mineral oil, silicone oils, dimethicone, isohexadecane, isododecane, diethylhexyl cyclohexane, and mixtures thereof. In some instances, emollient comprises or is chosen from dicaprylyl ether, isododecane, hydrocarbon, dimethicone and mixtures thereof. In other cases, the emollient includes non-silicone oils.

In some embodiments, the emollient may be a non-volatile ester oil. The non-volatile ester oil may preferably be chosen from:

(1) monoesters comprising between 18 and 40 carbon atoms in total, in particular the monoesters of formula $R_1COOR_2$ in which $R_1$ represents a linear or branched fatty acid residue comprising from 4 to 40 carbon atoms and $R_2$ represents a hydrocarbon-based chain, which is especially branched, containing from 4 to 40 carbon atoms, on condition that $R_1+R_2 \geq 18$, for instance cetostearyl octanoate, isononyl isononanoate, $C_{12}$ to $C_{15}$ alkyl benzoates, 2-ethylhexyl palmitate, octyldodecyl neopentanoate, 2-octyldodecyl stearate, 2-octyldodecyl erucate, isostearyl isostearate, 2-octyldodecyl benzoate, alcohol or polyalcohol octanoates, decanoates or ricinoleates, isopropyl myristate, isopropyl palmitate, butyl stearate, hexyl laurate, 2-ethylhexyl palmitate, 2-hexyldecyl laurate, 2-octyldecyl palmitate, 2-octyldodecyl myristate or 2-diethylhexyl succinate. Preferably, they are esters of formula $R_1COOR_2$ in which $R_1$ represents a linear or branched fatty acid residue containing from 4 to 40 carbon atoms and $R_2$ represents a hydrocarbon-based chain that is especially branched, containing from 3 to 40 carbon atoms provided that $R_1+R_2 \geq 18$. Preferably, the ester comprises between 18 and 40 carbon atoms in total. Preferred monoesters that may be mentioned include 2-ethylhexyl palmitate and isopropyl palmitate.

(2) diesters, especially comprising between 18 and 60 carbon atoms in total and in particular between 18 and 50 carbon atoms in total. It is especially possible to use diesters of dicarboxylic acids and of monoalcohols, preferably such as diisostearyl malate, or glycol diesters of monocarboxylic acids, such as neopentyl glycol diheptanoate or poly-2-glyceryl diisostearate;

(3) triesters, especially comprising between 35 and 70 carbon atoms in total, in particular such as triesters of a tricarboxylic acid, such as triisostearyl citrate, or tridecyl trimellitate, or glycol triesters of monocarboxylic acids such as poly-2-glyceryl triisostearate; and/or (4) tetraesters, especially with a total carbon number ranging from 35 to 70, such as pentaerythritol or polyglycerol tetraesters of a monocarboxylic acid, for instance pentaerythrityl tetrapelargonate, pentaerythrityl tetraisostearate, pentaerythrityltetraisononanoate, glyceryl tris(2-decyl)tetradecanoate, poly-2-glyceryl tetraisostearateor pentaerythrityl tetrakis(2-decyl)tetradecanoate.

In some embodiments, the emollient may include a hydrocarbon-based oil of plant origin, such as phytostearyl esters, such as phytostearyl oleate, phytostearyl isostearate and lauroyl/octyldodecyl/phytostearyl glutamate, triglycerides formed from fatty acid esters of glycerol, in particular in which the fatty acids may have chain lengths ranging from $C_4$ to $C_{36}$ and especially from $C_{18}$ to $C_{36}$, these oils possibly being linear or branched, and saturated or unsaturated; these oils may especially be heptanoic or octanoic triglycerides, shea oil, alfalfa oil, poppy oil, millet oil, barley oil, rye oil, candlenut oil, passionflower oil, shea butter, squalane, aloe vera oil, sweet almond oil, peach stone oil, groundnut oil, argan oil, avocado oil, baobab oil, borage oil, broccoli oil, calendula oil, camellina oil, canola oil, carrot oil, safflower oil, flax oil, rapeseed oil, cotton oil, coconut oil, marrow seed oil, wheatgerm oil, jojoba oil, lily oil, macadamia oil, corn oil, meadowfoam oil, St John's Wort oil, monoi oil, hazelnut oil, apricot kernel oil, walnut oil, olive oil, evening primrose oil, palm oil, blackcurrant pip oil, kiwi seed oil, grapeseed oil, pistachio oil, winter squash oil, pumpkin oil, quinoa oil, musk rose oil, sesame oil, soybean oil, sunflower oil, castor oil and watermelon oil, and mixtures thereof and mixtures thereof.

In some embodiments, the emollient may be a linear or branched hydrocarbons of mineral or synthetic origin, such as liquid paraffins and derivatives thereof, petroleum jelly, polydecenes, polybutenes, hydrogenated polyisobutene.

In some embodiments, the emollients may include at least one saturated, branched hydrocarbon, which may be of plant origin, having a carbon chain that is at least 20 carbons in length.

In some embodiments, the emollients may include a linear or branched hydrocarbon, a hydrocarbon-based oil of plant origin, a monoester, and a tetraester. In some embodiments, the emollients may include 2-8, 3-7-, or 4-6 emollients.

In some embodiments, the lip composition includes at least 40%, 45%, 50%, 55%, 60%, or 65% by weight of one or more emollients. In some embodiments, the lip composition includes at least 40% by weight of one or more emollients. In some embodiments, the lip composition includes at least 60% by weight of one or more emollients. In some embodiments, the lip composition includes at least 65% by weight of one or more emollients. In some embodiments, the lip composition includes a plurality of emollients, where one emollient is present in an amount of at least 30% by weight of the lip composition.

In some embodiments, the lip composition includes a plurality of emollients, where one emollient is present in an amount of at least 30% by weight of the lip composition, and the remaining emollients are present in a total amount of at least 20% or at least 30% by weight of the lip composition.

In some embodiments, the lip composition includes a plurality of emollients, where a first emollient is present in an amount of at least 30% by weight of the lip composition and a second emollient is present in an amount of at least 10% or at least 15% by weight. In some embodiments, the first emollient may be a linear or branched hydrocarbon. In some embodiments, the second emollient may be a monoester. In some embodiments, each emollient is present in an amount of at least 2%, at least 3%, or at least 4% by weight of the lip composition.

The emollients may include one or more ester oils in an amount of at least 25% by weight of the lip composition.

Waxes.

The waxes may include one or more soft waxes, and one or more hard waxes. "Soft waxes" may be defined as those waxes which have a melting point of below about 70° C., and preferably, a melting point of below about 60° C. "Hard waxes" may be defined as those waxes which have a melting point of equal to or greater than about 70° C., and preferably, a melting point of equal to or greater than about 60° C.

Non-limiting examples of soft waxes include paraffin wax, stearic alcohol, ozokerite, synthetic beeswax, beeswax, candelilla wax, PVP/eicosene copolymer, hydrogenated jojoba wax, palm butter, sumac wax, polyglyceryl beeswax, tricontanyl/PVP, siliconyl beeswax, stearyl stearate, ceresin wax, hydrogenated myristyl olive esters (e.g., phytowax olive 14 L 48), hydrogenated stearyl olive esters (e.g., phytowax olive 18 L 57), Koster K82P, orange peel wax, Pentaerythritol distearate, *Theobroma Grandiflorum* Seed Butter, silicone resin wax, Polymethylalkyl dimethylsiloxane, Pentaerythrityl tetrastearate, Tetracontanyl Stearate, fatty acid wax, behenyl alcohol, alkyl dimethicone wax, Stearyl Benzoate, Berry wax, koster wax, siliconyl candelilla wax, Ditrimethylolpropane tetrastearate, Clariant Licowax KST 1, Dipentaerythrytol hexastearate, Ditrimethylolpropane tetrabehenate, Behenyl methacrylate gréffé PDMS, jojoba esters, waxolive, inholive, phytowax ricin 16 L 64, hydrogenated macadamia seed oil, some synthetic waxes, dooctadecyl carbonate, montan wax, lemon peel extract, and ditrimethyloylpropane tetrastearate.

Non-limiting examples of hard waxes include carnauba wax, microcrystalline wax, polyethylene wax, hydrogenated castor oil, wax AC 540, Hydroxyoctacosanyl Hydroxystearate, hydrogenated castor wax, wax AC 400, rice bran wax, C20-40 alkyl stearate, Alcohol polyethylene wax, octanedioate, sunflower seed wax, fischer-tropsch wax, Chinese insect wax, shellac wax, benehyl fumarate, some synthetic waxes, betsawax RX-13750, phytowax ricin 22 L 73, and vegetable wax.

In some embodiments, the waxes include at least two soft waxes and at least two hard waxes. In some embodiments, the waxes include 2-8, 3-7, or 4-6 waxes. In some embodiments, the waxes include hard waxes in a total amount of at least 15%, at least 16%, at least 17%, at least 18%, at least 19%, or at least 20% by weight of the lip composition. In some embodiments, the weight ratio of hard waxes to soft waxes may be 10:1 to 15:1.

In some embodiment, the lip composition may include at least 20%, 21%, 22%, 23%, 24%, or 25% by weight of waxes. In some embodiment, the lip composition may include no more than 30% by weight of waxes.

Fillers.

As used herein, the term "filler" refers to colorless or white, mineral or organic, natural or synthetic solids (such as particles of any form), which are in a form that is insoluble and dispersed in the medium of the composition. The plurality of fillers includes silica silylate and cellulose. In some embodiments, the only fillers may be silica silylate and cellulose.

These fillers make it possible to give the composition containing them softness, a matt effect and uniformity of the makeup result. In addition, these fillers advantageously make it possible to combat various attacking factors such as sebum or sweat.

Non-limiting examples of fillers includes talc, mica, silica, kaolin, poly-b-alanine powder and polyethylene powder, powders of tetrafluoroethylene polymers (Teflon®), lauroyl lysine, starch, boron nitride, hollow polymer microspheres such as those of polyvinylidene chloride/acrylonitrile, acrylic acid copolymer microspheres, precipitated calcium carbonate, magnesium carbonate, magnesium hydrogen carbonate, hydroxyapatite, barium sulfate, aluminum oxides, polyurethane powders, composite fillers, hollow silica microspheres, and glass or ceramic microcapsules. In some embodiments, the fillers may include silica silylate, nylon-12, cellulose, methacrylate crosspolymer, or a combination thereof.

In some embodiments, the fillers may be present in a total amount of up to 6.5%, 6%, or 5.5% by weight of the composition.

In some embodiments, the weight ratio of cellulose to silica silylate is 2.5:1 to 3.5:1.

In some embodiments, the filler may be substantially free, essentially free, or free of perlite. In some embodiments, the filler may be substantially free, essentially free, or free of clays (including, e.g., kaolin). In some embodiments, the filler may be substantially free, essentially free, or free of ceramic beads. In some embodiments, the filler may be substantially free, essentially free, or free of talc and mica.

In some embodiments, the filler may be substantially free, essentially free, or free, of silica and hydrated silica.

The lip composition may be substantially free, essentially free, or free of water and silicones (e.g., a polymer comprising a siloxane). The lip composition may be substantially free, essentially free, or free of beeswax. The lip composition may be vegan. As used herein, the term "vegan" refers to a product including, but not limited to foods and supplements, which are not made from or with the aid of animals or animal products (including products from living animals).

Coloring Agent (Colorant).

In some embodiments, the lip composition may include at least one coloring agent. The at least one coloring agent may preferably chosen from pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, surface-treated mica, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the coloring agent(s) should be present in a total amount of no more than 5% by weight of the lip composition. In some embodiments, the coloring agent(s) are present in a total amount of no more than 4%, no more than 3.5%, or no more than 3% by weight of the composition.

In some embodiments, the coloring agents are primarily pigments, with all other colorants being present in a total amount of less than 1%, 0.9%, 0.8%, 0.7%, 0.6%, or 0.5% by weight of the lip composition.

In some embodiments, the coloring agents may be provided in an amount such that a ratio of the total amount (by weight) of the fillers to the total amount (by weight) of coloring agents from 2:1 to 1.5:1 is achieved.

Other Components.

The lip composition may include any other additive, excipient, or active ingredient used in cosmetics or personal care products. Non-limiting examples include, e.g., gelling/thickening agents, antioxidants, preservatives, surfactants, fragrances, UV-screening agents or UV filters, and/or vitamins and derivatives thereof.

In some embodiments, the lip composition may be substantially free of all other components (aside from the emollients, coloring agents, waxes, and fillers). In some embodiments, the other components are present in a total amount of less than 0.9%, 0.8%, 0.7%, 0.6%, 0.5%, or 0.4% by weight of the lip composition.

In one preferred embodiment, The lip composition may include: (i) at least 40% by weight of one or more emollients; (ii) at least 20% by weight of waxes, the waxes including a hard wax and a soft wax; (iii) not more than 6% by weight of fillers, the fillers consisting of silica silylate and cellulose; (iv) not more than 5% by weight of one or more coloring agents; and (v) less than 0.5% by weight of other components, such as one or more additives or excipients.

In various embodiments, a method of providing a low coverage and matte finish to lips may be provided. The method may include applying an embodiment of the lip composition as disclosed herein to the lips.

In various aspects, a lip product may be provided. The lip product may include a glass or polymeric container having a main body and a cap or lid. A lip composition as disclosed herein may be disposed within the main body of the container. In some embodiments, the lip product may be a lipstick, a lip liner, or a lip balm.

Example 1

Dozens of test formulas were used to test the impact of different filler combinations. Each test formula had a general formula matching the description in Table 1, below.

TABLE 1

(General Formulations)

| Material | % by weight |
| --- | --- |
| Emollient 1 (hydrocarbon-based oil of plant origin) | 3-5% |
| Emollient 2 (hydrocarbon-based oil of plant origin) | 3-5% |
| Emollient 3 (saturated, branched hydrocarbon, of plant origin, having a carbon chain that is at least 20 carbons in length) | 30-40% |
| Emollient 4 (monoester) | 4-5% |
| Emollient 5 (monoester) | 11-16% |
| Emollient 6 (tetraester) | 0 or 8-10% |
| Total Waxes | 14-25% |
| Hard Waxes | 13-23% |
| Soft Waxes | 1-2% |
| Filler | 4.5-25% |
| Coloring Agent | 0-3% |
| All Other | 0-0.5% |

Various filler systems (e.g., one or more fillers in combination) were tested, and evaluated in terms of texture, comfort, and finish.

TABLE 2

(Partial Table Of Evaluations)

| Total % By Weight of Filler System | Filler System | Evaluation Results |
| --- | --- | --- |
| 25% | Hollow Sphere Silica - 25% | Finish too satin. |
| 20% | Amorphous Silica - 4% Hollow Sphere Silica - 15% Silica Silylate - 1% | Finish too satin. |
| 23.5% | Perlite - 19% Hollow Sphere Silica - 4% Silica Silylate - 0.5% | Uncomfortable, Gritty Feel. |
| 20% | Amorphous Silica - 19% Silica Silylate - 1% | Draggy, Uncomfortable, Finish too satin. |
| 23.81% | Amorphous Silica - 17.86% Hollow Sphere Silica - 4.76% Silica Silylate - 1.19% | Draggy, Uncomfortable. |
| 20.50% | Perlite - 5% Amorphous Silica - 14.5% Silica Silylate - 1% | Draggy, Uncomfortable. |
| 20% | Amorphous Silica - 12% Hollow Sphere Silica - 4% | Draggy, Uncomfortable. |

TABLE 2-continued (Partial Table Of Evaluations)

| Total % By Weight of Filler System | Filler System | Evaluation Results |
|---|---|---|
| | Silica Silylate - 1% Perlite - 3% | |
| 20% | Perlite - 3% Amorphous Silica - 17% | Draggy, Uncomfortable. |
| 20% | Amorphous Silica - 12% Perlite - 3% Cellulose - 5% | Draggy, Uncomfortable. |
| 12% | Amorphous Silica - 5% Perlite - 3% Cellulose - 4% | Draggy, Uncomfortable. |
| 8% | Perlite - 8% | Gritty feel, Finish too satin. |
| 6% | Perlite - 3% Cellulose - 3% | Insufficient mattity. |
| 6% | Silica Silylate - 1% Perlite - 5% | Insufficient mattity. |
| 4.5% | Silica Silylate - 1.5% Perlite - 3% | Insufficient mattity. |
| 5% | Silica Silylate - 1% Cellulose - 4% | Acceptable. |
| 5.5% | Silica Silylate - 1.5% Cellulose - 4% | Acceptable. |

Surprisingly, it is clear that the specific combination of silica silylate and cellulose are required to provide the necessary use characteristics (comfort, soft matte finish).

Example 2

An embodiment of a lip composition as disclosed herein can be seen in Table 3, below.

TABLE 3

(Exemplary Composition)

| Material | % by weight |
|---|---|
| Total Emollients | 63-77% |
| Emollient 1 (hydrocarbon-based oil of plant origin) | 4-5% |
| Emollient 2 (hydrocarbon-based oil of plant origin) | 3-4% |
| Emollient 3 (saturated, branched hydrocarbon, of plant origin, having a carbon chain that is at least 20 carbons in length) | 30-35% |
| Emollient 4 (monoester) | 4-5% |
| Emollient 5 (monoester) | 14-18% |
| Emollient 6 (tetraester) | 8-10% |
| Total Waxes | 20-23% |
| Hard Waxes (3) | 19-21% |
| Soft Waxes (1) | 1-2% |
| Total Fillers | 5-6% |
| Silica Silylate | 1-2% |
| Cellulose | 4-5% |
| Total Coloring Agents | 2-3% |
| Pigments (4) | 2.25-2.75% |
| Dyes/Lakes (2) | 0.25-0.75% |
| All Other | 0.2-0.4% |

Various modifications may be made to the various aspects disclosed herein, such modifications being contemplated as being within the scope of the invention. For example, while a specific order of steps or arrangement of functional elements is presented in the various embodiments described herein, various other orders/arrangements of steps or functional elements may be utilized within the context of the various embodiments. Further, while modifications to embodiments may be discussed individually, various embodiments may use multiple modifications contemporaneously or in sequence, compound modifications and the like.

Although various embodiments which incorporate the teachings of the present invention have been shown and described in detail herein, those skilled in the art can readily devise many other varied embodiments that still incorporate these teachings. Thus, while the foregoing is directed to various embodiments of the present invention, other and further embodiments of the invention may be devised without departing from the basic scope thereof. As such, the appropriate scope of the invention is to be determined according to the claims.

What is claimed is:

1. A lip composition comprising:
   one or more emollients;
   waxes, the waxes including a hard wax and a soft wax; and
   a plurality of fillers including silica silylate and cellulose;
   wherein the lip composition is anhydrous and free of silicones.

2. The lip composition according to claim 1, further comprising a coloring agent, where the coloring agent is present in a total amount not more than 5% by weight of the lip composition.

3. The lip composition according to claim 2, wherein the coloring agent is present in a total amount not more than 3% by weight of the lip composition.

4. The lip composition according to claim 1, wherein the plurality of fillers are present in a total amount of not more than 6% by weight of the lip composition.

5. The lip composition according to claim 4, wherein the plurality of fillers consist of silica silylate and cellulose.

6. The lip composition according to claim 1, wherein the one or more emollients are present in a total amount of not less than 60% by weight of the lip composition.

7. The lip composition according to claim 1, wherein the one or more emollients include at least one saturated, branched hydrocarbon having a carbon chain that is at least 20 carbons in length.

8. The lip composition according to claim 1, wherein the one or more emollients include one or more ester oils in an amount of at least 25% by weight of the lip composition.

9. The lip composition according claim 1, wherein:
   the one or more emollients are present in a total amount of at least 40% by weight of the lip composition;
   the waxes are present in a total amount of at least 20% by weight of the lip composition.

10. The lip composition according to claim 9, wherein the lip composition is a vegan composition.

11. The lip composition according to claim 1, wherein the lip composition is essentially free of silica.

12. The lip composition according to claim 1, wherein the lip composition is free of perlite.

13. The lip composition according to claim 1, wherein the lip composition is free of beeswax.

14. A method of providing a low coverage and matte finish to lips, comprising:
   applying the lip composition of claim 1 to the lips.

15. A lipstick product, comprising:
   a glass or polymeric container having a main body and a cap or lid; and
   a lip composition according to claim 1, wherein the lip composition is disposed within the main body of the glass or polymeric container.

* * * * *